United States Patent
Katayama et al.

(10) Patent No.: US 8,252,557 B2
(45) Date of Patent: Aug. 28, 2012

(54) PEPTIDE-CONTAINING CULTURE MEDIUM FOR CULTURING ANIMAL CELL

(75) Inventors: Satoshi Katayama, Tokyo (JP); Shouhei Kishishita, Tokyo (JP); Kunihiko Kodaira, Tokyo (JP); Makoto Sadamitsu, Tokyo (JP); Yoshinori Takagi, Tokyo (JP); Hiroki Matsuda, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/998,494

(22) PCT Filed: Oct. 27, 2009

(86) PCT No.: PCT/JP2009/068360
§ 371 (c)(1),
(2), (4) Date: Apr. 27, 2011

(87) PCT Pub. No.: WO2010/050448
PCT Pub. Date: May 6, 2010

(65) Prior Publication Data
US 2011/0207174 A1 Aug. 25, 2011

(30) Foreign Application Priority Data

Oct. 28, 2008 (JP) ................................. 2008-276843

(51) Int. Cl.
*C12P 21/04* (2006.01)
*C12N 5/00* (2006.01)
(52) U.S. Cl. ........................................ 435/71.1; 435/404
(58) Field of Classification Search ................ 260/112.5; 435/71.1, 404
See application file for complete search history.

(56) References Cited

U.S. PATENT DOCUMENTS
4,235,772 A 11/1980 Lundin et al.

FOREIGN PATENT DOCUMENTS
EP 2 154 244 A1 2/2010
WO WO 2008/136398 A1 11/2008

OTHER PUBLICATIONS

International Search Report mailed Nov. 24, 2009, in PCT/JP2009/068360, 2 pages.
Dukic-Stefanovic et al., "Characterization of antibody affinities using an AGE-modified dipeptide spot library," Journal of Immunological Methods, 2002, 266:45-52.
Franek et al., "Specific Effects of Synthetic Oligopeptides on Cultured Animal Cells," Biotechnol. Prog., 2002, 18:155-158.
Franek et al., "Survival Factor-Like Activity of Small Peptides in Hybridoma and CHO Cells Cultures," Biotechnol. Prog., 2005, 21:96-98.
Franek et al., "Enhancement of Monoclonal Antibody Production by Lysine-Containing Peptides," Biotechnol. Prog., 2003, 19(1):169-174.
Ito et al., "The Growth-Stimulating Activity of Peptides on Human Hematopoietic Cell Cultures," Experimental Cell Research, 1969, 56:10-14.
Kuwae et al., "Development of a Fed-Batch Culture Process for Enhanced Production of Recombinant Human Antithrombin by Chinese Hamster Ovary Cells," Journal of Bioscience and Bioengineering, 2005, 100(5):502-510.
McGrath et al., "Structure-Guided Design of Peptide-Based Tryptase Inhibitors," Biochemistry, 2006, 45:5964-5973.

*Primary Examiner* — Maryam Monshipouri
(74) *Attorney, Agent, or Firm* — Foley & Lardner LLP

(57) ABSTRACT

Disclosed is a culture medium for culturing an animal cell, which is characterized by containing a peptide comprising, as a constituent unit, an amino acid residue selected from the amino acid group consisting of serine, tyrosine and cysteine. The culture medium is suitable for the high level production of a protein by an animal cell.

20 Claims, 8 Drawing Sheets

PEPTIDE-CONTAINING CULTURE MEDIUM FOR CULTURING ANIMAL CELL

CROSS-REFERENCE TO RELATED APPLICATIONS

This application is a National Stage application of PCT/JP2009/068360, filed Oct. 27, 2009, which claims priority from Japanese application JP 2008-276843, filed Oct. 28, 2008.

This application is a 371 of PCT/JP2009/068360, filed Oct. 27, 2009, which claims priority to Japanese application 2008-276843 filed Oct. 28, 2008.

TECHNICAL FIELD

The present invention relates to serum-free or low-serum cell culture, and particularly relates to a culture medium suitable for high-throughput production of a protein (for example, a protein capable of serving as an active ingredient of a drug) by animal cells (for example, CHO cells). Further, the present invention relates to a method of culturing animal cells and thereby producing a protein, using such a culture medium.

BACKGROUND ART

In order to obtain a natural-type protein produced by animal cells through culturing the animal cells or in order to produce a desired protein through culturing animal cells to which a gene encoding the desired protein has been introduced, the culture medium usually contains an extract from mammals for supporting proliferation of these animal cells, in addition to basic nutrients, such as salts, saccharides, amino acids, and vitamins. Specifically, serum such as fetal bovine serum is added to a culture medium in an amount of 5 to 20%. Such serum derived from a mammal accounts for 75 to 95% of the total cost of the medium, and has a disadvantage that stable proliferation is not achieved due to a lot-to-lot variation in quality. In addition, a mammal-derived serum a cannot be sterilized by, for example, an autoclave; thus, it is likely of undergoing contamination with viruses or mycoplasma. Even though many of them are harmless, the contamination may be an additional unknown factor from the viewpoint of stable production.

Recently, it has been concerned about alleged involvement of extracts from mammals with, for example, mad cow disease, bovine spongiform encephalopathy (BSE), transmissible spongiform encephalopathy (TSE), or Creutzfeld-Jakob disease (CJD), and there is a demand for culture media not containing extracts from mammals for culturing animal cells, from the viewpoint of safety. In addition, serum contains 500 or more different proteins, resulting in complication of isolation and purification of a desired protein produced by the cells, from the culture medium.

In order to solve the above-described problems, serum-free culture media have been developed for culturing animal cells in the absence of serum. In methods for serum-free culture, serum-free culture solutions have been developed that contains plasma proteins such as fetuin, transferrin, and albumin; hormones such as steroid hormones and insulin; growth factors; and nutritional factors such as amino acids and vitamins, as alternatives to serum.

Proteins used in serum-free culture, such as fetuin, insulin, transferrin, and a growth factor, are purified from serum or are produced as recombinant proteins from recombinant organisms. The use of these proteins still has disadvantages such as, for example, inclusion of substances derived from living organisms, even in trace amounts, use of expensive materials, and a lot-to-lot variation in culture.

Recently, serum-free culture using protein hydrolysates has also been developed, but this also has the same disadvantages, i.e., inclusion of substances derived from living organisms, high cost, and a lot-to-lot variation in the products obtained. Thus, the methods are not satisfactory for production of useful proteins.

Accordingly, there is a demand for a culture method using a synthetic culture medium that contains the minimum amount of substances derived from living organisms, is inexpensive, is with a small lot-to-lot variation, and can enhance production of a large amount of protein. Recently, analysis of behavior of glucose and amino acids in culture solutions in fed-batch culture has revealed that addition of an increased amount of glutamic acid to the fed-batch culture contributes to high throughput production of antithrombin (NPL 1). Unfortunately, these findings are based on only studies on CHO cells expressing glutamine synthetase, and validation has not been conducted with normal CHO cells. Furthermore, there is no finding on individual amino acids other than glutamic acid. In addition, the throughput of protein production is still insufficient. Accordingly, there is a high demand for culture using a synthetic culture medium that further increases the throughput.

Since the fed-batch culture involves supply of nutrients that have been consumed by cells proliferating and surviving in the culture medium while the culture medium is generally not drawn out from a batch until the completion of the culture, the osmotic pressure of the culture medium gradually increases mainly due to an acid or base added for the pH adjustment. An excessive increase in osmotic pressure is harmful for cells. Saccharides and amino acids serving as nutrients in the culture medium and by-products generated by metabolism also cause an increase in osmotic pressure.

Also reported is a method for increasing a desired product by addition of a specific peptide to the culture medium (NPL 2).

CITATION LIST

Non Patent Literature

NPL 1: Journal of Bioscience and Bioengineering (2005), 100 (5), 502-510
NPL 2: Biotechnol. Prog (2003), 19, 169-174

SUMMARY OF INVENTION

Technical Problem

Accordingly, it is an object of the present invention to provide an improved serum-free or low-serum culture technology, using a new material capable of exerting similar effects as those of living organisms-derived substances as a substitute for such substances, to thereby solve the disadvantages due to conventional culture medium components.

Solution To Problem

The present inventors have solved the above-described problems by using a peptide as a novel component of a culture solution. The peptide comprises a combination of specific amino acids.

The present application provides the following inventions:

(1) An animal cell culture medium comprising a peptide consisting of 10 or fewer amino acids, or a salt thereof, wherein the peptide includes at least two kinds of amino acids selected from the group consisting of serine, tyrosine, and cysteine;

(2) The animal cell culture medium according to aspect (1), wherein (a) the animal cell culture medium comprises a peptide consisting of 10 or fewer amino acids, wherein the total amount of serine, tyrosine, and cysteine accounts for at least 33%; or (b) the animal cell culture medium comprises a peptide consisting of 10 or fewer amino acids, wherein the total amount of two kinds of amino acids selected from the group consisting of serine, tyrosine, and cysteine accounts for at least 33%;

(3) An animal cell culture medium comprising a tripeptide comprising serine, tyrosine, and cysteine, or a salt thereof;

(4) An animal cell culture medium comprising a dipeptide comprising two kinds of amino acids selected from the group consisting of serine, tyrosine, and cysteine, or a salt thereof;

(5) A method of culturing cells for producing a desired protein, comprising culturing cells capable of producing the protein using a culture solution containing the animal cell culture medium according to any one of aspects (1) to (4);

(6) A method of producing a desired protein, comprising culturing cells capable of producing the protein using the animal cell culture medium according to any one of aspects (1) to (4);

(7) The method according to aspect (5) or (6), wherein the animal cell culture medium is added at the start of culture or is added in a fed-batch or continuous manner;

(8) The method according to aspect (5) or (6), wherein the cells are cultured by batch culture, repeated batch culture, fed-batch culture, repeated fed-batch culture, continuous culture, or perfusion culture;

(9) The method according to aspect (8), wherein the cells are cultured by fed-batch culture;

(10) The method according to aspect (9), wherein the animal cell culture medium is supplied to the culture solution by continual feeding repeated a plurality of times or continuous feeding;

(11) The method according to aspect (5) or (6), wherein the cells are transfected with a gene encoding a desired protein;

(12) The method according to aspect (11), wherein the desired protein is an antibody;

(13) The method according to aspect (5) or (6), wherein the cells are mammal cells;

(14) The method according to aspect (13), wherein the mammal cells are CHO cells;

(15) A method for producing a drug, comprising producing a protein serving as an active ingredient by the method according to aspect (6);

(16) A peptide consisting of two or three amino acids comprising at least two kinds of amino acids selected from the group consisting of serine, tyrosine, and cysteine, wherein (a) the peptide comprises serine, tyrosine, and cysteine; or the peptide comprises serine, tyrosine, and cysteine of which at least one is optionally chemically modified; or (b) the peptide comprises two kinds of amino acids selected from serine, tyrosine, and cysteine; or the peptide comprises two kinds of amino acids selected from serine, tyrosine, and cysteine of which at least one is optionally chemically modified;

(17) A method of enhancing throughput of protein production by animal cells during culture, comprising adding the peptide according to aspect (16) to a culture solution;

(18) The method according to aspect (17), wherein the culture solution contains the peptide according to aspect (16) in an amount of about 0.1 to about 25 mM;

(19) An additive to be added to a serum-free culture medium for culturing animal cells, comprising the peptide according to aspect (16); and

(20) An agent of enhancing throughput of protein production by transformed cells, comprising the peptide according to aspect (16).

Advantageous Effects of Invention

The present invention enables enhanced high-throughput of protein production by maintaining the survival rate of cells during the cell culture, using a synthetic medium that does not contain biological substances. Furthermore, the synthetic medium contains an ultrahigh-purity synthetic peptide or peptide derived from a recombinant protein; thus, the components in the composition are apparent, which provides uniform culture media with a small lot-to-lot variation. Consequently, a homogeneous protein can be produced, which is advantageous for industrial manufacture. Accordingly, the present invention is highly useful in the preparation of bioactive peptides or proteins. For example, the present invention can significantly contribute to mass supply of antibodies for pharmaceutical use.

DESCRIPTION OF EMBODIMENTS

Figure 1:
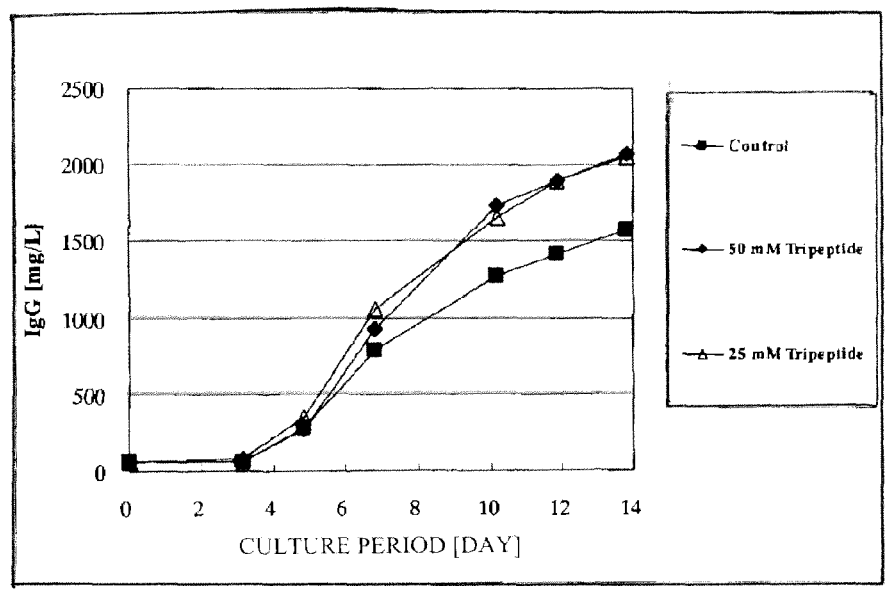
FIG. 1 shows transition of the antibody concentration during culture in a medium containing a peptide (Example 1).

Embodiments of the present invention will be described in more detail below.

1. Medium

The animal cell culture medium according to the present invention is characterized by comprising a peptide of from 2 to 10 amino acid residues, having specific kinds of amino acids as monomeric units that constitute the peptide. The present invention is characterized in that the specific kinds of constituent amino acids include at least two kinds of amino acids selected from the group consisting of three kinds of amino acids, i.e. serine, tyrosine, and cysteine.

The animal cell culture medium according to the present invention will be referred to as "peptide-containing culture medium" or simply "culture medium", throughout the following description, as a matter of convenience.

In the present invention, the term "peptide-containing culture medium" refers not only to a culture medium comprising the above-described peptide as an initial culture medium but also to a medium being prepared so as to contain the above-described peptide in the culture solution by addition of a fed-batch medium (i.e., ultimately prepared as a culture solution).

The present inventors previously analyzed the behavior of amino acids during serum-free culture and found out that certain specific amino acids tend to restrict survival of cultured cells and protein expression. Among such amino acids, the inventors focused on serine, tyrosine, and cysteine, and filed a patent application (a co-pending application: PCT/JP2008/058046) directed to a method of culturing animal cells using a culture medium containing these amino acids alone or in combination in a high concentration. After that, the present inventors have predicted that, as compared to direct addition of these amino acids to a culture medium, addition of a peptide composed of these amino acids to the culture medium may ameliorate an increase in osmolar pressure. Furthermore, making serine, tyrosine, and cysteine into a peptide according to the present invention leads to improved solubility of tyrosine as a constituent of the peptide, although tyrosine by itself has a particularly low solubility (the solubility of tyrosine is usually about 2.1 mM at 20° C. and about 4.1 mM at 40° C.). Consequently, by virtue of this peptidization, a culture medium can contain a peptide containing tyrosine in a relatively high concentration of 50 mM or more, which allows tyrosine to be added to, for example, a fed-batch medium in a significantly higher concentration than ever before. In addition, since an enhanced throughput of cell production due to addition of a specific peptide to the culture medium is recognized, the peptide-containing culture medium according to the present invention exhibits enhanced protein production by the cells.

The appropriate concentration of the peptide in a culture solution varies depending on types of cells and conditions for culture. Accordingly, a lower limit of the concentration of the peptide in a culture medium is the level allowing cells to survive as a minimum requirement, a suitable concentration is the level allowing significantly enhanced expression of a protein compared to that of a fundamental culture medium, and an upper limit is the level allowing substantially no production of undesirable harmful metabolites. Typically, a concentration of the peptide in the peptide-containing culture medium according to the present invention is in the range of about 0.1 to about 100 mM, preferably about 0.2 to about 50 mM, and more preferably about 0.5 to about 25 mM, as the final concentration in a culture solution.

Other components in the culture medium may be those usually used in animal cell culture media, and examples thereof include amino acids, vitamins, lipid factors, energy sources, osmo-regulators, iron sources, and pH buffers. In addition to these components, for example, a trace metal element, a surfactant, a proliferation cofactor, and a nucleoside may be contained. Such culture medium components, including the peptide composed of specific kinds of amino acids, may be separately added to a cell culture medium. Specifically, for example, a high concentration of peptide and culture medium components may be added to the cell culture at the same time or at different times.

Specific examples of the other components in the culture medium include amino acids, such as L-alanine, L-arginine, L-asparagine, L-asparaginic acid, L-glutamine, L-glutamic acid, glycine, L-histidine, L-isoleucine, L-leucine, L-lysine, L-methionine, L-ornithine, L-phenylalanine, L-proline, L-threonine, L-triptophane, and L-valine, preferably, L-alanine, L-arginine, L-asparagine, L-asparaginic acid, L-glutamine, L-glutamic acid, glycine, L-histidine, L-isoleucine, L-leucine, L-lysine, L-methionine, L-phenylalanine, L-proline, L-threonine, L-triptophane, and L-valine; vitamins, such as i-inositol, biotin, folic acid, lipoic acid, nicotine amide, nicotinic acid, p-aminobenzoic acid, calcium pantothenate, pyridoxal hydrochloride, pyridoxine hydrochloride, riboflavin, thiamine hydrochloride, vitamin B12, and ascorbic acid, preferably, biotin, folic acid, lipoic acid, nicotine amide, calcium pantothenate, pyridoxal hydrochloride, riboflavin, thiamine hydrochloride, vitamin B12, and ascorbic acid; lipid factors, such as choline chloride, choline tartrate, linoleic acid, oleic acid, and cholesterol, preferably, choline chloride; energy sources, such as glucose, galactose, mannose, and fructose, preferably, glucose; osmo-regulators, such as sodium chloride, potassium chloride, and potassium nitrate, preferably, sodium chloride; iron sources, such as EDTA iron, iron citrate, ferrous chloride, ferric chloride, ferrous sulfate, ferric sulfate, and ferric nitrate, preferably, ferric chloride, EDTA iron, and iron citrate; and pH buffers, such as sodium hydrogen carbonate, calcium chloride, sodium dihydrogen phosphate, HEPES, and MOPS, preferably, sodium hydrogen carbonate.

In addition to these components, the culture medium may further contain, for example, trace amounts of metal elements, such as copper sulfate, manganese sulfate, zinc sulfate, magnesium sulfate, nickel chloride, tin chloride, magnesium chloride, and/or sodium silicite, preferably, copper sulfate, zinc sulfate, and/or magnesium sulfate; a surfactant, such as Tween 80 or Pluronic F68; a proliferation cofactor, such as recombinant insulin, recombinant IGF, recombinant EGF, recombinant FGF, recombinant PDGF, recombinant TGF-α, ethanolamine hydrochloride, sodium selenite, retinoic acid, or putrescine hydrochloride, preferably, sodium selenite, ethanolamine hydrochloride, recombinant IGF, or putrescine hydrochloride; and a nucleoside, such as deoxyadenosine, deoxycytidine, deoxyguanosine, adenosine, cytidine, guanosine, or uridine. In the above-described preferred embodiments of the present invention, the culture medium may contain an antibiotic, such as streptomycin, penicillin G potassium, or gentamicin; and a pH indicator, such as phenol red.

The contents of the other components in the culture medium may be appropriately determined depending on the kind of cells to be cultured and the kind of a desired protein, and, preferably, the amino acid is in the range of 0.05 to 1500 mg/L, the vitamin is in the range of 0.001 to 10 mg/L, the lipid factor is in the range of 0 to 200 mg/L, the energy source is in the range of 1 to 20 g/L, the osmo-regulator is in the range of 0.1 to 10000 mg/L, the iron source is in the range of 0.1 to 500 mg/L, the pH buffer is in the range of 1 to 10000 mg/L, the trace metal element is in the range of 0.00001 to 200 mg/L, the surfactant is in the range of 0 to 5000 mg/L, the proliferation cofactor is in the range of 0.05 to 10000 μg/L, and the nucleoside is in the range of 0.001 to 50 mg/L.

The pH of the culture medium varies depending on cells to be cultured, but is usually 6.8 to 7.6, and is 7.0 to 7.4 in many cases.

The peptide-containing culture medium according to the present invention, preferably, does not contain serum derived from mammals.

The peptide-containing culture medium according to the present invention can be prepared by adding a peptide containing the above-described specific kinds of amino acids to a synthetic complete medium containing the above-described common components, or can be prepared using a known animal cell culture medium as a fundamental culture medium supplied with the above-described peptide. Examples of commercially available fundamental culture medium as the animal cell culture medium include, but not limited to, D-MEM (Dulbecco's Modified Eagle Medium), D-MEM/F-12 1:1 Mixture (Dulbecco's Modified Eagle Medium: Nutrient Mixture F-12), RPMI 1640, CHO-S-SFMII (Invitrogen), CHO-SF (Sigma-Aldrich), EX-CELL 301 (JRH biosciences), CD-CHO (Invitrogen), IS CHO-V (Irvine Scientific), and PF-ACF-CHO (Sigma-Aldrich). In culturing cells by fed-batch culture, such a commercially available culture media can be used as an initial culture medium, which is used at the first stage of cell culture. In such a case, a culture medium prepared by supplementing the above-described peptide to a high-concentration initial culture medium can be used as a fed-batch medium.

2. Peptide

The peptide used in the peptide-containing culture medium of the present application will now be described in detail. The peptide in the peptide-containing culture medium of the present application has a combination of specific kinds of constituent amino acids and may be a synthetic or recombinant-protein-derived peptide consisting of 2 to 10 amino acid residues. The combination of the amino acids is characterized in that at least two kinds of amino acids selected from the group consisting of serine, tyrosine, and cysteine are contained, as described above. The peptide of the present invention may further contain other kinds of amino acid in addition to serine, tyrosine, and cysteine. Further, the peptide of the present invention may contain a chemically modified amino acid. A specific embodiment includes:

(1) a peptide consisting of at most 10 residues of amino acids and comprising at least two kinds of amino acids selected from the group consisting of serine, tyrosine, and cysteine, or a salt thereof;

(2) a peptide consisting of at most 10 residues of amino acids and comprising serine, tyrosine, and cysteine in a total amount of at least 33% of the peptide, or a salt thereof; or (3) a peptide consisting of at most 10 residues of amino acids and comprising two kinds of amino acids selected from the group consisting of serine, tyrosine, and cysteine in a total amount of at least 33% of the peptide, or a salt thereof.

A more specific embodiment includes a peptide consisting of two or three amino acids or chemically modified amino acids, such as (4) a tripeptide comprising serine, tyrosine, and cysteine, or a salt thereof;

(5) a dipeptide comprising two kinds of amino acids selected from the group consisting of serine, tyrosine, and cysteine, or a salt thereof;

(6) a tripeptide comprising serine, tyrosine, and cysteine, at least one of which amino acids is optionally chemically modified, or a salt thereof; and (7) a peptide comprising two kinds of amino acids selected from serine, tyrosine, and cysteine, at least one of which amino acids is optionally chemically modified, or a salt thereof.

Examples of the tripeptide include Cys-Tyr-Ser, Ser-Cys-Tyr, and Tyr-Ser-Cys.

The peptides can be produced in a large amount by a process such as chemical synthesis or expression through a recombinant DNA technology. Specifically, in the chemical synthesis, a peptide having a specific sequence or a random sequence can be produced by binding artificial or chemically modified amino acids through a synthetic reaction. In the recombinant DNA technology, a desired peptide can be yielded by producing a protein containing a plurality of peptide sequences from a recombinant, purifying the protein, and enzymatically or chemically decomposing the protein into peptides. In particular, it is well known to persons skilled in the art that amino acids serving, for example, as a sequence for purification, a spacer, or an enzymatic cleavage site are inserted in order to produce a peptide of the present invention in a large amount at a low cost by enzymatic digestion of a recombinant protein.

The term "chemical modification of an amino acid" used in the present invention refers to a chemical modification that will not cause a significant change in the activity of a peptide containing the chemically modified amino acid. For example, modification of C-terminal (e.g., amide, ester, or acyl), modification of N-terminal (e.g., acetyl), and modification of a non-natural amino acid (e.g., norleucine) are included.

3. Cell Culture

The peptide-containing culture medium according to the present application is significantly useful for culturing animal cells capable of producing a protein.

More specifically, a culture solution comprising the peptide-containing culture medium according to the present application can be used when producing a desired protein by culturing cells that can produce the protein, for example, in acquisition of a natural protein produced by animal cells through culturing thereof or in production of a desired protein through culturing animal cells transfected with a gene encoding the desired protein.

In conventional serum-free culture, culture media must contain plasma proteins, hormones, and growth factors, as an alternative to serum. However, in the present application, a peptide-containing culture medium, which is prepared only by adding a peptide comprised of specific kinds of amino acid residues to a fundamental culture medium, can maintain a high survival rate of cells to further increase throughput of protein production by the cells, without addition of the biological components.

In general, cell culture is classified into batch culture, continuous culture, and fed-batch culture. In the present invention, any culture can be employed, but the fed-batch culture or the continuous culture is preferably employed, and the fed-batch culture is most preferred.

The batch culture is a process that allows cells to grow by addition of a small amount of a seed culture solution to the culture medium, without addition of a fresh medium during culturing or without discharge of the culture medium used for the culture. If the batch culture is employed in the present invention, a peptide-containing culture medium is used as the seed culture solution.

The continuous culture is a culturing process that involves continuous addition of a fresh medium and continuous discharge of the medium used for the culture. Note that perfusion culture is also classified into the continuous culture.

The fed-batch culture is a method positioned between the batch culture and the continuous culture and is also called semi-batch culture. The fed-batch culture is a culturing process that involves continuous or consecutive addition of a fresh medium without continuous discharge of the medium used for the culture, unlike the continuous culture. The culture medium to be added during the fed-batch culture (hereinafter, referred to as fed-batch medium) is not necessarily the same as that of the culture medium that has been used for the culture (hereinafter, referred to as initial culture medium); hence, a different medium or only a specific component may be fed.

The initial culture medium in the present invention is, in general, a culture medium that is used at the first stage of cell culture. However, if the fed-batch medium is added dividedly in several times, the medium before addition of the fed-batch medium at each time may be defined as the initial culture medium. Cells can be cultured using the above-described peptide-containing culture medium as the initial culture medium. The concentration of the peptide is determined so as to enhance the production of a desired protein in the initial culture medium. For example, the concentration is preferably in the range of about 0.1 to 50 mM and more preferably about 0.5 to 25 mM.

If the fed-batch culture or the continuous culture is employed in the present invention, the peptide-containing culture medium can be used as the culture medium to be added during the culture. It is desirable that the culture medium (fed-batch medium) to be added during the fed-batch culture has a high concentration so that the culture volume will not highly increase.

If the fed-batch culture is employed as the cell culture in the present invention, the peptide concentration can be determined so as to enhance the production of a desired protein by continuous or consecutive addition of a fed-batch medium containing the peptide in a high concentration to the culture medium during the culture. Specifically, for example, the fed-batch medium containing about 1 to 1000 mM, preferably about 10 to 500 mM, and most preferably about 20 to 100 mM of a peptide can be used. In the examples described below, CHO cells were cultured by the fed-batch culture. In each example, a fed-batch medium containing the peptide was added in a concentration, a volume, and at a time that allow the cells to produce an increased amount of a desired protein.

The amount of the fed-batch medium to be added to a culture medium in the present invention is 1 to 150%, preferably 5 to 50%, and most preferably 8 to 20% of the amount of the initial culture medium, and the fed-batch medium may be added continuously, or for a certain period, or gradually over the entire culture period.

The method of culture of the present invention is not particularly limited, and can be applied to culture of various animal cells, for example, COS cells or CHO cells that have been transfected with a gene encoding a desired protein by genetic engineering or hybridoma cells, represented by mouse-human, mouse-mouse, and mouse-rat hybridoma cells, which produce antibodies. The method of the present invention can be applied to obtain a natural protein that is produced by animal cells through culturing the animal cells, or also can be applied to culture cells other than the above-mentioned cells, such as BHK cells and HeLa cells.

In the present invention, most preferred animal cells are CHO cells transfected with a gene encoding a desired protein. The desired protein is not particularly limited and may be any protein, such as antibodies, e.g., a natural antibody, an antibody fragment, a low-molecular-weight antibody, a chimeric antibody, a humanized antibody (for example, an anti-IL-6 receptor antibody, an anti-glypican-3 antibody, an anti-CD3 antibody, an anti-CD20 antibody, an anti-GPIIb/IIIa antibody, an anti-TNF antibody, an anti-CD25 antibody, an anti-EGFR antibody, an anti-Her2/neu antibody, an anti-RSV antibody, an anti-CD33 antibody, an anti-CD52 antibody, an anti-IgE antibody, an anti-CD11a antibody, an anti-VEGF antibody, and an anti-VLA4 antibody); and physiologically active proteins (e.g., granulocyte colony-stimulating factor (G-CSF), granulocyte-macrophage colony-stimulating factor (GM-CSF), erythropoietin, interferon, interleukins such as IL-1 and IL-6, t-PA, urokinase, serum albumin, and a blood coagulation factor). In particular, preferred are antibodies that can be used as drugs.

Conditions for the culture can be optimized according to the type of the cells to be cultured. For example, CHO cells are usually cultured under an atmosphere of a gas phase at a $CO_2$ concentration of 0 to 40%, preferably 2 to 10%, at 30 to 39° C., preferably about 37° C., for 1 to 50 days, preferably 1 to 14 days.

The animal cells can be cultured using various types of culture systems, such as a fermentation culture tank, an air-lift culture system, a culture flask, a spinner flask, a micro carrier culture system, a fluidized-bed culture system, a hollow-fiber culture system, a roller-bottle culture system, and a packed-bed culture system.

4. Production of Protein

A large amount of a protein can be produced through culture of animal cells by the above-described cell culture. Therefore, the method of producing a desired protein by culturing cells capable of producing the protein, using the peptide-containing culture medium of the present application, is also one embodiment of the present invention.

In general, in some cases, proteins are produced by merely culturing animal cells, and in other some cases, special procedures are necessary. Such procedures and conditions may be appropriately determined according to the animal cells to be cultured. For example, CHO cells that have been transformed with a vector containing a gene encoding a mouse-human chimeric antibody by genetic engineering can give a desired protein in a culture medium through the culture under the above-described conditions for 1 to 50 days, preferably 5 to 21 days, and most preferably 7 to 14 days. The desired protein can be isolated and purified according to a routine process (for example, see Kotai Kogaku Nyumon (Introduction of antibody engineering), Chijin Shokan, (1994) pp. 102-104; and Affinity Chromatography Principles & Methods, GE Healthcare, (2003) pp. 56-60).

According to the present invention, it is possible to produce a large amount of a recombinant antibody (e.g., a natural antibody, an antibody fragment, a low-molecular-weight antibody, a chimeric antibody, a humanized antibody, and a bispecific antibody); and a recombinant protein (e.g., granulocyte colony-stimulating factor (G-CSF), granulocyte-macrophage colony-stimulating factor (GM-CSF), erythropoietin, interferon, interleukin such as IL-1 or IL-6, t-PA, urokinase, serum albumin, and a blood coagulation factor).

Examples of the antibody produced by the method according to the present invention include not only monoclonal antibodies derived from animals such as human, mouse, rat, hamster, rabbit, and monkey but also artificially modified recombinant antibodies such as chimeric antibodies, humanized antibodies, and bispecific antibodies. The immunoglobulin class of each antibody is not particularly limited, and the class may be any of IgG (such as IgG1, IgG2, IgG3, and IgG4), IgA, IgD, IgE, and IgM, but IgG and IgM are preferred in the case where they are used as pharmaceutical drugs. In addition, the antibody of the present invention may be a whole antibody or a low-molecular-weight antibody such as an antibody fragment (e.g., Fv, Fab, or F(ab)$_2$) or a monovalent or divalent single-chain Fv (e.g., scFv or sc(Fv)$_2$) having a variable region of an antibody linked with a linker such as a peptide linker.

5. Pharmaceuticals

If a protein or a polypeptide (also called a protein of the present invention) produced by the method of the present invention has a biological activity capable of being used as a medical drug, the drug can be formulated by mixing the protein or polypeptide with a pharmaceutically acceptable carrier or additive. The protein of the present invention and the drug containing the protein of the present invention as an active ingredient are also included in the scope of the present invention.

Examples of the pharmaceutically acceptable carrier and additive include water, pharmaceutically acceptable organic solvents, collagen, polyvinyl alcohol, polyvinylpyrrolidone, carboxyvinyl polymers, sodium carboxymethyl cellulose, sodium polyacrylate, sodium arginate, water-soluble dextran, sodium carboxymethyl starch, pectin, methyl cellulose, ethyl cellulose, xanthan gum, gum Arabic, casein, agar, polyethylene glycol, diglycerin, glycerin, propylene glycol, vaseline, paraffin, stearyl alcohol, stearic acid, human serum albumin (HSA), mannitol, sorbitol, lactose, and surfactants acceptable as pharmaceutical additives.

In actual cases, the additives are selected from the above-mentioned additives according to the formulation of a therapeutic agent as a drug of the present invention and may be used alone or in appropriate combination, but are not limited thereto. For example, in an injection formulation, a purified polypeptide is dissolved in a solvent, such as physiological saline, a buffer solution, or a glucose solution, and an adsorption inhibitor, such as Tween 80, Tween 20, gelatin, or human serum albumin, is added thereto. Alternatively, a lyophilized formulation for dissolving and reconstituting it before use can be also used. Examples of an excipient for the lyophilization include sugar alcohols, such as mannitol and glucose, and saccharides.

The effective amount of the polypeptide is appropriately determined depending on, for example, the type of a polypeptide, the type of disease to be treated or prevented, the age of a patient, and seriousness of disease. For example, if the protein of the present invention is an anti-glypican antibody, the effective amount ranges from 0.001 to 1000 mg for 1 kg of body weight as a single dose. Alternatively, the amount may range from 0.01 to 100000 mg/body for one patient. However, the dose is not limited thereto.

The administration route may be either oral or parenteral, but preferred is parenteral administration, specifically, injection (for example, systemic or local administration through, e.g., intravenous injection, intramuscular injection, intraperitoneal injection, or subcutaneous injection), nasal administration, pulmonary administration, or percutaneous administration.

6. Use of Peptide

The method of producing a protein according to the present invention is, in other words, a method of providing improvement in a protein yield obtainable from animal cells that are being cultured, by adding a peptide described in the present application to the culture solution. Accordingly, the peptide of the present invention that is characterized by at least two kinds of amino acids selected from the group consisting of three kinds of amino acids, i.e., serine, tyrosine, and cysteine, can be used as an additive for serum-free culture media for animal cells or a potentiating agent for protein production by transformed cells.

The present invention will be specifically described with reference to examples and reference examples below. Note that these examples merely describe the present invention and are not intended to limit the scope of the present invention.

Example 1

Antibody-Producing Fed-Batch Culture Using Tripeptide-Containing Fed-Batch Medium (CHO Cell Line Transfected with Antibody Gene)

Culture medium compositions and their preparation processes are as follows:

Initial culture medium: a commercially available animal cell culture medium was subjected to dissolution and filtration sterilization for use as an initial culture medium.

Fed-batch media: a fed-batch medium (control) was prepared by dissolving the commercially available animal cell culture medium into a concentration three-fold higher than that of the initial culture medium and then sterilizing the medium by filtration. Tripeptide-containing fed-batch media (50 mM tripeptide and 25 mM tripeptide) were prepared by adding a tripeptide to the fed-batch medium into a final concentration of 50 mM and 25 mM, respectively, and then sterilizing the tripeptide-containing media by filtration.

Tripeptide: a tripeptide having a sequence of Cys-Tyr-Ser was chemically synthesized.

Cell: humanized IgG (anti-glypican-3 antibody)-producing CHO cell line (see International Patent Publication No. WO 2006/006693).

Figure 2:
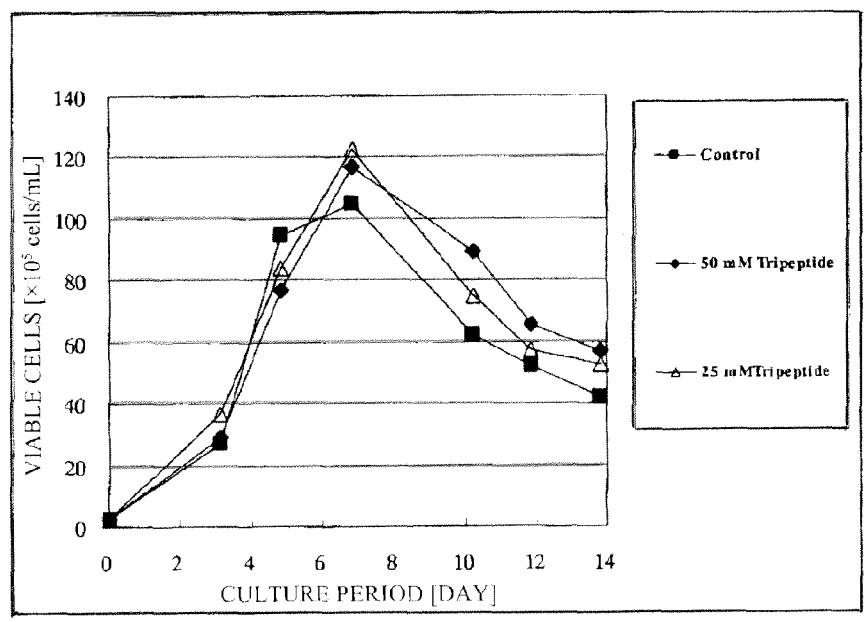
FIG. 2 shows transition of the number of viable cells during culture in a medium containing a peptide (Example 1).
Figure 3:
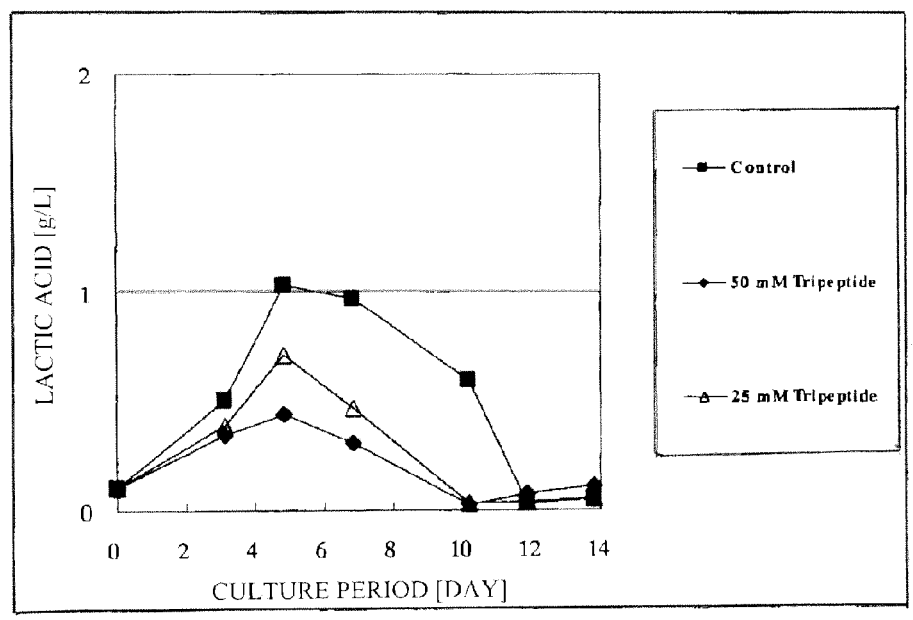
FIG. 3 shows transition of the lactic acid concentration during culture in a medium containing a peptide (Example 1).

The initial culture medium was placed in a jar-type cell culture system, and then the CHO cell line was added thereto into a concentration of $2 \times 10^5$ cells/mL and was cultured under the conditions of 37° C. and 10% $CO_2$. During the culture period of 14 days, a pH level of not lower than 7.0 and a dissolved oxygen level of 40% were automatically maintained. The fed-batch medium was continuously fed from the 3rd day to the 14th day of the culture at a constant flow rate (1.0 g/hr for 1 L of the initial culture medium). The culture medium was sampled at the start of the culture and on the 3rd, 5th, 7th, 10th, 12th, and 14th days. The number of viable cells in each sampled culture solution was counted by trypan blue staining. The antibody concentration in the centrifuged supernatant of each culture solution was measured by affinity chromatography using protein A, and the concentration of lactic acid was measured by an immobilized enzyme process. As shown in FIG. 1, in the fed-batch culture (control) using the fed-batch medium not containing the tripeptide, the antibody concentration after the 14-day culture was about 1.6 g/L. In contrast, in the fed-batch culture (50 mM tripeptide and 25 mM tripeptide) using the fed-batch medium containing 50 mM or 25 mM of the tripeptide, the antibody concentrations after the 14-day culture were both about 2.1 g/L. Thus, an antibody concentration higher by about 30% was achieved. FIG. 2 shows transition of the number of viable cells during the culture. In addition, as shown in FIG. 3, the concentration of lactic acid in the fed-batch culture using the fed-batch media containing the tripeptide varied at relatively low levels from the 3rd day to the 10th day of the culture, compared to that in the fed-batch culture using the fed-batch medium not containing the tripeptide.

Example 2

Antibody-Producing Fed-Batch Culture Using Dipeptide-Containing Fed-Batch Medium (CHO Cell Line Transfected with Antibody Gene)

Culture medium compositions and their preparation processes are as follows:

Initial culture medium: a commercially available animal cell culture medium was subjected to dissolution and filtration sterilization for use as an initial culture medium.

Fed-batch media: a fed-batch medium (control) was prepared by dissolving the commercially available animal cell culture medium into a concentration three-fold higher than that of the initial culture medium and then sterilizing the medium by filtration. A dipeptide-containing fed-batch medium (dipeptide) was prepared by adding a dipeptide to the fed-batch medium into a final concentration of 50 mM and then sterilizing the dipeptide-containing medium by filtration.

Dipeptide: a dipeptide having a sequence of Cys-Tyr was chemically synthesized.

Cell: humanized IgG (anti-glypican-3 antibody)-producing CHO cell line (see International Patent Publication No. WO 2006/006693) was used.

Figure 4:
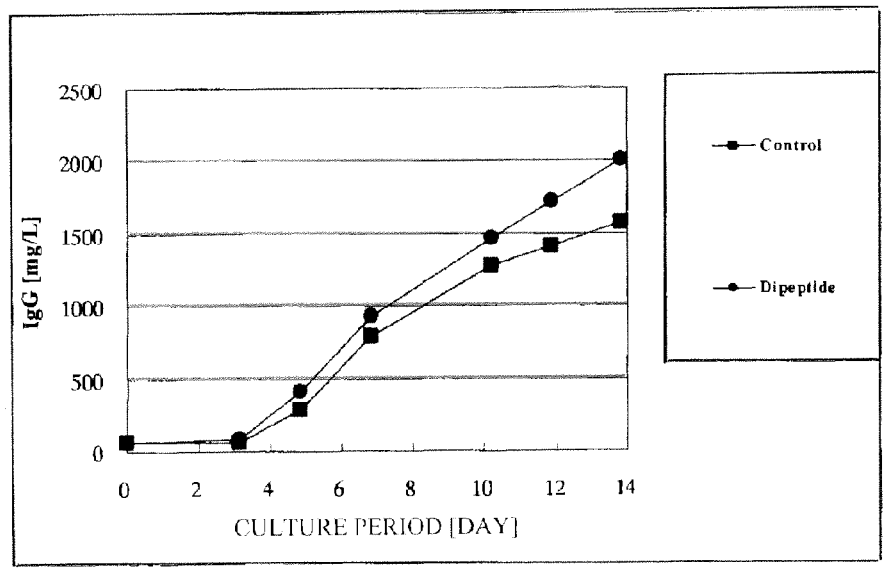
FIG. 4 shows transition of the antibody concentration during culture in a medium containing a peptide (Example 2).
Figure 5:
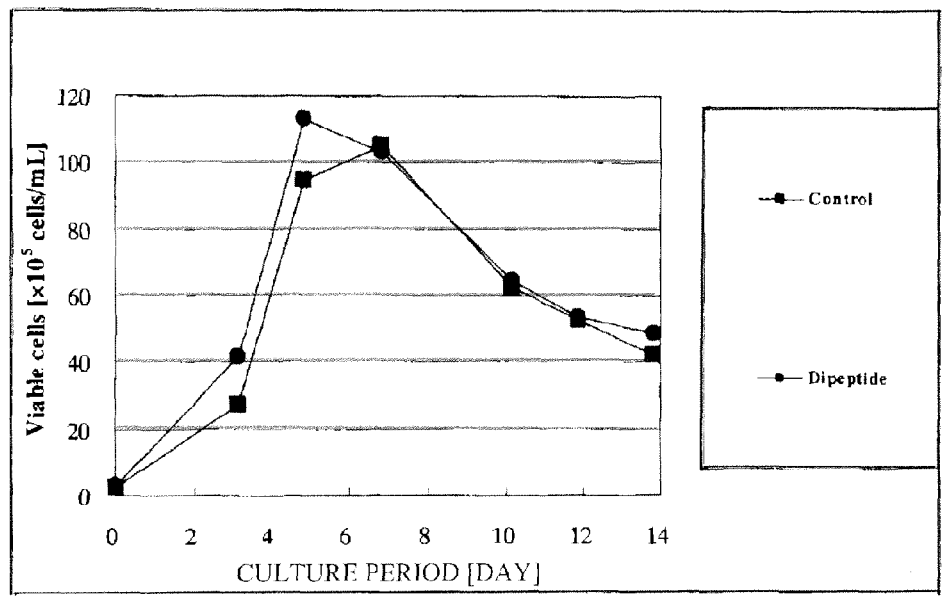
FIG. 5 shows transition of the number of viable cells during culture in a medium containing a peptide (Example 2).
Figure 6:
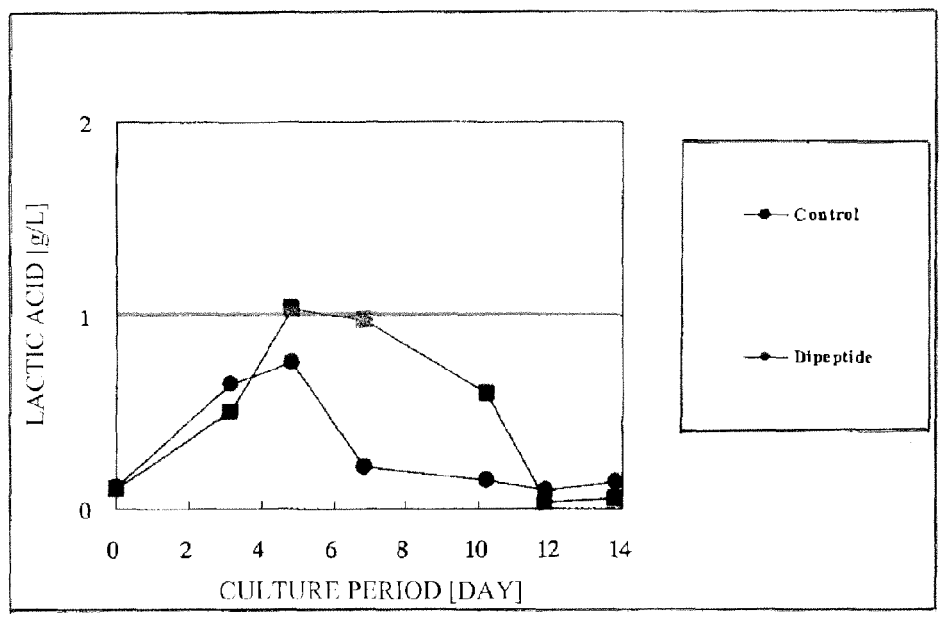
FIG. 6 shows transition of the lactic acid concentration during culture in a medium containing a peptide (Example 2).

The initial culture medium was placed in a jar-type cell culture system, and then the CHO cell line was added thereto into a concentration of $2 \times 10^5$ cells/mL and was cultured under the conditions of 37° C. and 10% $CO_2$. During the culture period of 14 days, a pH level of not lower than 7.0 and a dissolved oxygen level of 40% were automatically maintained. The fed-batch medium was continuously fed from the 3rd day to the 14th day of the culture at a constant flow rate (1.0 g/hr for 1 L of the initial culture medium). The culture medium was sampled at the start of the culture and on the 3rd, 5th, 7th, 10th, 12th, and 14th days. The number of viable cells in each sampled culture solution was counted by trypan blue staining. The antibody concentration in the centrifuged supernatant of each culture solution was measured by affinity chromatography using protein A, and the concentration of lactic acid was measured by an immobilized enzyme process. As shown in FIG. 4, in the fed-batch culture (control) using the fed-batch medium not containing the dipeptide, the antibody concentration after the culture for the 14-day culture was about 1.6 g/L. In contrast, in the fed-batch culture (50 mM dipeptide) using the fed-batch medium containing 50 mM of the dipeptide, the antibody concentration after the 14-day culture was both about 2.0 g/L. Thus, an antibody concentration higher by about 25% was achieved. FIG. 5 shows transition of the number of viable cells during the culture. In addition, as shown in FIG. 6, the concentration of lactic acid in the fed-batch culture using the fed-batch medium containing the dipeptide varied at relatively low levels from the 5th day to the 10th day of the culture, compared to that in the fed-batch culture using the fed-batch medium not containing the dipeptide.

The following Reference Examples 1 to 3 will show the culture using culture media containing amino acids in high concentrations, which is described in unpublished copending PCT/JP2008/058046 filed by the present inventors.

Reference Example 1

Fed-Batch Culture Using Low-pH Fed-Batch Medium Containing Serine, Cysteine, and Tyrosine in High Concentrations (CHO Cell Line Transfected with Antibody Gene)

Culture medium compositions and their preparation processes are as follows:

Initial culture medium: a commercially available animal cell culture medium was subjected to dissolution and filtration sterilization for use as an initial culture medium.

Fed-batch medium: a fed-batch medium was prepared by dissolving the animal cell culture medium in a concentration three-fold higher than that of the initial culture medium; 50 mM of serine, 1.8 mM of cysteine hydrochloride monohydrate, and 14.5 mM of tyrosine were added to the animal cell culture medium; hydrochloric acid was added to the culture medium to reduce the pH level (around pH 1.5) until the culture medium components were completely dissolved; and, after confirmation of complete dissolution of the culture medium components, the culture medium was sterilized by filtration.

Cell: humanized IgG (anti-glypican-3 antibody)-producing CHO cell line (see International Patent Publication No. WO 2006/006693).

Figure 7:
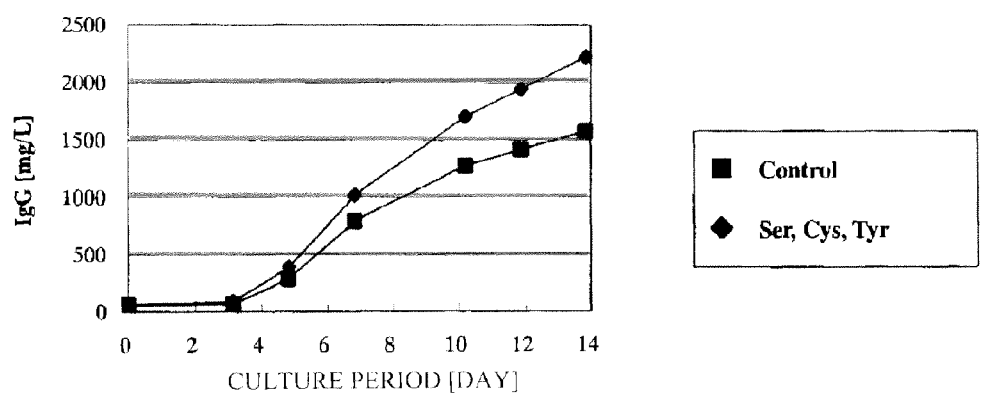
FIG. 7 shows transition of the antibody concentration during culture in a medium containing amino acids in high concentrations (Reference Example 1).
Figure 8:
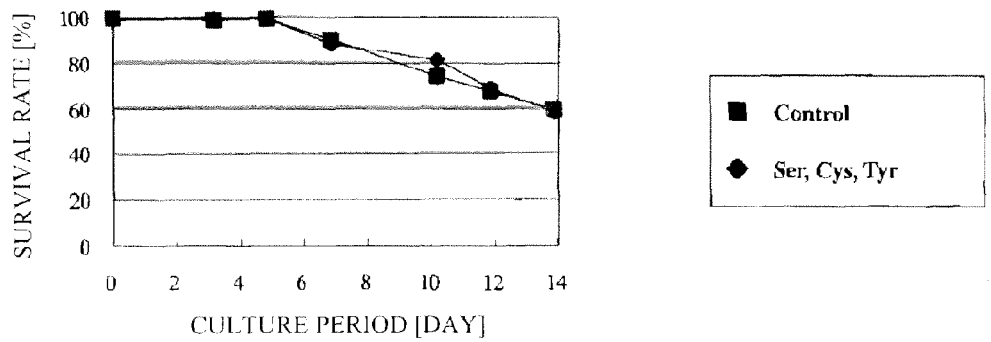
FIG. 8 shows transition of the survival rate during culture in a medium containing amino acids in high concentrations (Reference Example 1).
Figure 9:
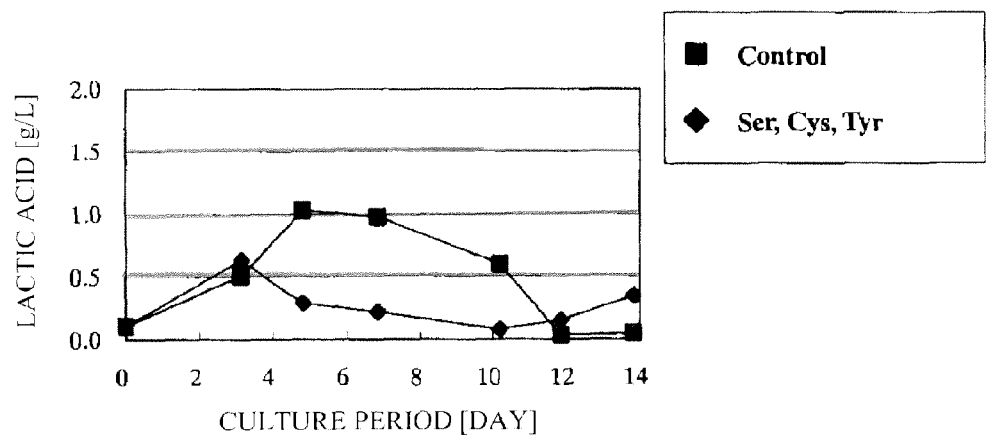
FIG. 9 shows transition of the lactic acid concentration during culture in a medium containing amino acids in high concentrations (Reference Example 1).

The initial culture medium was placed in a jar-type cell culture system, and then the CHO cell line was added thereto into a concentration of $2 \times 10^5$ cells/mL and was cultured under the conditions of 37° C. and 10% $CO_2$. During the culture period of 14 days, a pH level of not lower than 7.0 and a dissolved oxygen level of 40% were automatically maintained. The fed-batch medium was continuously fed from the 3rd day to the 14th day of the culture at a constant flow rate (1.0 g/hr for 1 L of the initial culture medium). The culture medium was sampled at the start of the culture and on the 3rd, 5th, 7th, 10th, 12th, and 14th days. The concentration of the produced antibody in the supernatant of each culture sample was measured by affinity chromatography using protein A; the survival rate was measured by trypan blue staining; and the concentration of lactic acid was measured by an immobilized enzyme process. As shown in FIG. 7, in the fed-batch culture (control) using the fed-batch medium to which serine, cysteine, and tyrosine were not enriched, the antibody concentration after the 14-day culture was about 1.6 g/L, while, in the fed-batch culture (Ser, Cys, Tyr) using the low-pH fed-batch medium to which serine, cysteine, and tyrosine were enriched, the antibody concentration after the 14-day culture was about 2.2 g/L. Thus, an antibody concentration higher by about 40% was achieved. FIG. 8 shows transition of the survival rate during the culture. In addition, as shown in FIG. 9, the concentration of lactic acid in the fed-batch culture using the low-pH fed-batch medium to which serine, cysteine, and tyrosine were enriched varied at low levels during the culture after the 3rd day, compared to that in the fed-batch culture using the fed-batch medium to which serine, cysteine, and tyrosine were not enriched.

Reference Example 2

Fed-Batch Culture Using Low-pH Fed-Batch Medium Containing Serine, Cysteine, and Tyrosine in High Concentrations (CHO Cell Line Transfected with Antibody Gene and Hamster Taurine Transporter Gene)

Culture medium compositions and their preparation processes are as follows:

Initial culture medium: a commercially available animal cell culture medium was subjected to dissolution and filtration sterilization for use as an initial culture medium.

Fed-batch medium: a fed-batch medium was prepared by dissolving the animal cell culture medium in a concentration three-fold higher than that of the initial culture medium; 50 mM of serine, 1.8 mM of cysteine hydrochloride monohydrate, and 14.5 mM of tyrosine were added to the animal cell culture medium; hydrochloric acid was added to the culture medium to reduce the pH level (around pH 1.5) until the culture medium components were completely dissolved; and, after confirmation of complete dissolution of the culture medium components, the culture medium was sterilized by filtration.

Cell: humanized IgG-producing CHO cell line transfected with a taurine transporter gene (see International Patent Publication No. WO 2007/119774).

Figure 10:
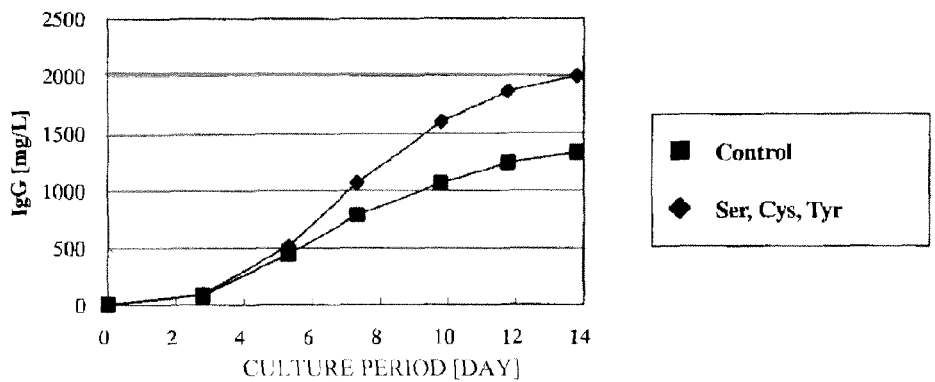
FIG. 10 shows transition of the antibody concentration during culture in a medium containing amino acids in high concentrations (Reference Example 2).
Figure 11:
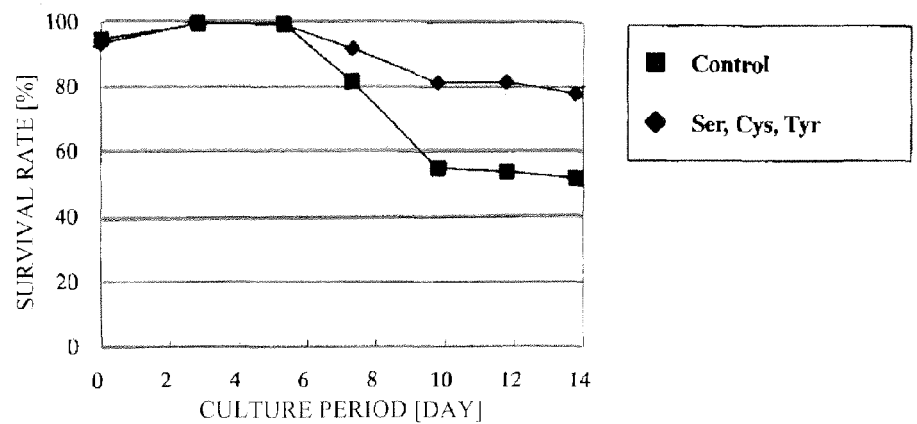
FIG. 11 shows transition of the survival rate during culture in a medium containing amino acids in high concentrations (Reference Example 2).
Figure 12:
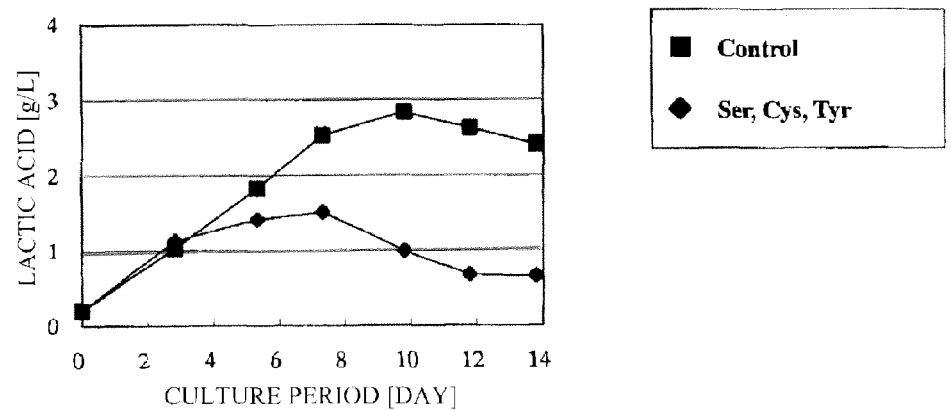
FIG. 12 shows transition of the lactic acid concentration during culture in a medium containing amino acids in high concentrations (Reference Example 2).

The initial culture medium was placed in a jar-type cell culture system, and then the CHO cell line was added thereto into a concentration of $2\times10^5$ cells/mL and was cultured under the conditions of 37° C. and 10% $CO_2$. During the culture period of 14 days, a pH level of not lower than 7.0 and a dissolved oxygen level of 40% were automatically maintained. The fed-batch medium was continuously fed from the 3rd day to the 14th day of the culture at a constant flow rate (1.5 g/hr for 1 L of the initial culture medium). The culture medium was sampled at the start of the culture and on the 3rd, 5th, 7th, 10th, 12th, and 14th days. The concentration of the produced antibody in the supernatant of each culture sample was measured by affinity chromatography using protein A; the survival rate was measured by trypan blue staining; and the concentration of lactic acid was measured by an immobilized enzyme process. As shown in FIG. 10, in the fed-batch culture (control) using the fed-batch medium to which serine, cysteine, and tyrosine were not enriched, the antibody concentration after the 14-day culture was about 1.3 g/L, while, in the fed-batch culture (Ser, Cys, Tyr) using the low-pH fed-batch medium to which serine, cysteine, and tyrosine were enriched, the antibody concentration after the 14-day culture was about 2.0 g/L. Thus, an antibody concentration higher by about 54% was achieved. As shown in FIG. 11, in the fed-batch culture (control) using the fed-batch medium to which serine, cysteine, and tyrosine were not enriched, the survival rate after the 14-day culture was 52%, while, in the fed-batch culture (Ser, Cys, Tyr) using the low-pH fed-batch medium to which serine, cysteine, and tyrosine were enriched, the survival rate after the 14-day culture was 78%. Thus, a high survival rate was maintained. Furthermore, as shown in FIG. 12, the concentration of lactic acid in the fed-batch culture (Ser, Cys, Tyr) using the low-pH fed-batch medium to which serine, cysteine, and tyrosine were enriched varied at low levels during the culture after the 3rd day, compared to that in the fed-batch culture (control) using the fed-batch medium to which serine, cysteine, and tyrosine were not enriched.

Reference Example 3

Fed-Batch Culture for Confirming Contribution of Serine, Cysteine, and Tyrosine in High Concentrations to High Throughput of Antibody Production (CHO Cell Line Transfected with Antibody Gene and Hamster Taurine Transporter Gene)

Culture medium compositions and their preparation processes are as follows:

Initial culture medium: a commercially available animal cell culture medium was subjected to dissolution and filtration sterilization for use as an initial culture medium.

Fed-batch medium (Ser, Cys, Tyr): a fed-batch medium was prepared by dissolving the animal cell culture medium into a concentration three-fold higher than that of the initial culture medium; 50 mM of serine, 1.8 mM of cysteine hydrochloride monohydrate, and 14.5 mM of tyrosine were added to the animal cell culture medium; hydrochloric acid was added to the culture medium to reduce the pH level (around pH 1.5) until the culture medium components were completely dissolved; and, after confirmation of complete dissolution of the culture medium components, the culture medium was sterilized by filtration.

Fed-batch medium (Ser, Cys): a fed-batch medium was prepared by dissolving the animal cell culture medium into a concentration three-fold higher than that of the initial culture medium; 50 mM of serine and 1.8 mM of cysteine hydrochloride monohydrate were added to the animal cell culture medium; hydrochloric acid was added to the culture medium to reduce the pH level (around pH 1.0) until the culture medium components were completely dissolved; and, after confirmation of complete dissolution of the culture medium components, the culture medium was sterilized by filtration.

Fed-batch medium (Ser, Tyr): a fed-batch medium was prepared by dissolving the animal cell culture medium into a concentration three-fold higher than that of the initial culture medium; 50 mM of serine and 14.5 mM of tyrosine were added to the animal cell culture medium; hydrochloric acid was added to the culture medium to reduce the pH level (around pH 1.0) until the culture medium components were completely dissolved; and, after confirmation of complete dissolution of the culture medium components, the culture medium was sterilized by filtration.

Fed-batch medium (Cys, Tyr): a fed-batch medium was prepared by dissolving the animal cell culture medium into a concentration three-fold higher than that of the initial culture medium; 1.8 mM of cysteine hydrochloride monohydrate and 14.5 mM of tyrosine were added to the animal cell culture medium; hydrochloric acid was added to the culture medium to reduce the pH level (around pH 1.0) until the culture medium components were completely dissolved; and, after confirmation of complete dissolution of the culture medium components, the culture medium was sterilized by filtration.

Cell: humanized IgG-producing CHO cell line transfected with a taurine transporter gene.

Figure 13:
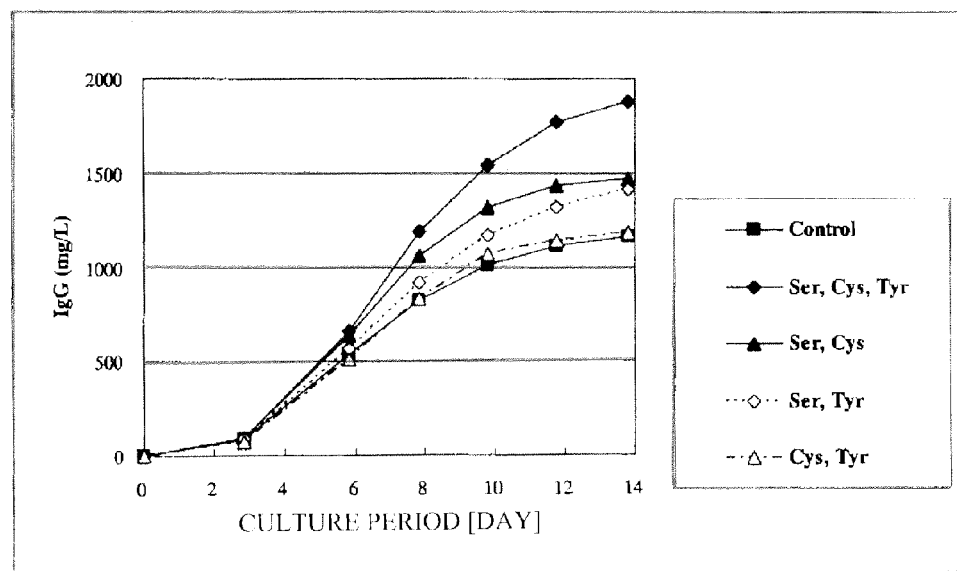
FIG. 13 shows transition of the antibody concentration during culture in a medium containing amino acids in high concentrations (Reference Example 3).

The initial culture medium was placed in a jar-type cell culture system, and then the CHO cell line was added thereto into a concentration of $2\times10^5$ cells/mL and was cultured under the conditions of 37° C. and 10% $CO_2$. During the culture period of 14 days, a pH level of not lower than 7.0 and a dissolved oxygen level of 40% were automatically maintained. The fed-batch medium was continuously fed from the 3rd day to the 14th day of the culture at a constant flow rate (1.5 g/hr for 1 L of the initial culture medium). The culture medium was sampled at the start of the culture and on the 3rd, 5th, 7th, 10th, 12th, and 14th days. The concentration of the produced antibody in the supernatant of each culture sample was measured by affinity chromatography using protein A. The amino acid concentrations of serine and tyrosine were measured by amino acid analysis using an ion-exchange column. As shown in FIG. 13, in the fed-batch culture (control) using the fed-batch medium to which serine, cysteine, and tyrosine were not enriched, the antibody concentration after the 14-day culture was about 1.16 g/L. In contrast, the results of antibody concentration measurement were: in the fed-batch culture (Ser, Cys, Tyr) using the low-pH fed-batch medium to which serine, cysteine, and tyrosine were enriched, the antibody concentration after the 14-day culture was 1.87 g/L; in the fed-batch culture (Ser, Cys) using the low-pH fed-batch medium to which serine and cysteine were enriched, the antibody concentration after the 14-day culture was 1.47 g/L; in the fed-batch culture (Ser, Tyr) using the low-pH fed-batch medium to which serine and tyrosine were enriched, the antibody concentration after the 14-day culture was 1.41 g/L; and in the fed-batch culture (Cys, Tyr) using the low-pH fed-batch medium to which cysteine and tyrosine were enriched, the antibody concentration after the 14-day culture was 1.18 g/L. Accordingly, the results suggest that high-concentration serine, cysteine, and tyrosine, in this order, contribute to high throughput of antibody production. The results also suggest that simultaneous addition of high-concentration serine, cysteine, and tyrosine to a fed-batch medium most contribute to high throughput of antibody production.

Figure 14:
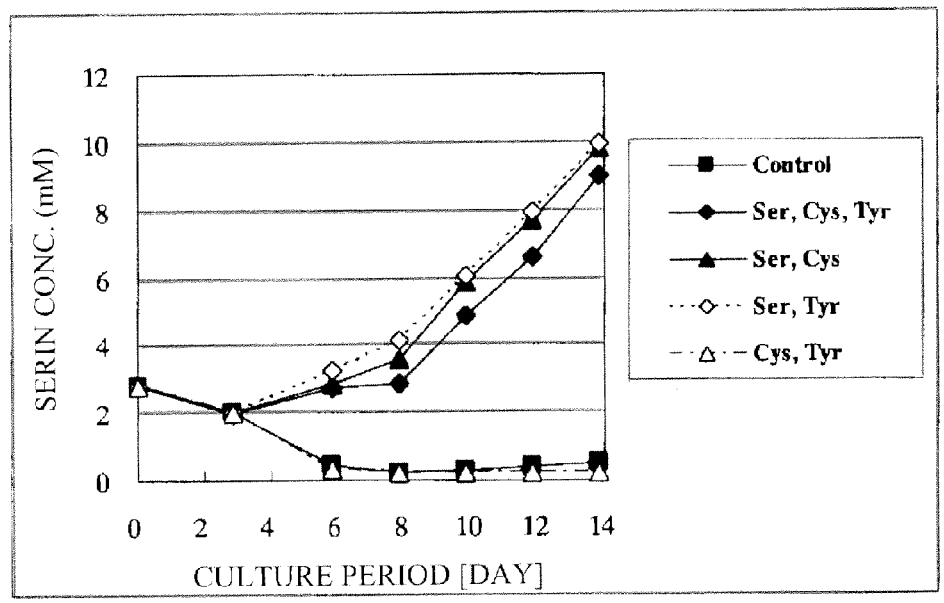
FIG. 14 shows transition of the serine concentration during culture in a medium containing amino acids in high concentrations (Reference Example 3).
Figure 15:
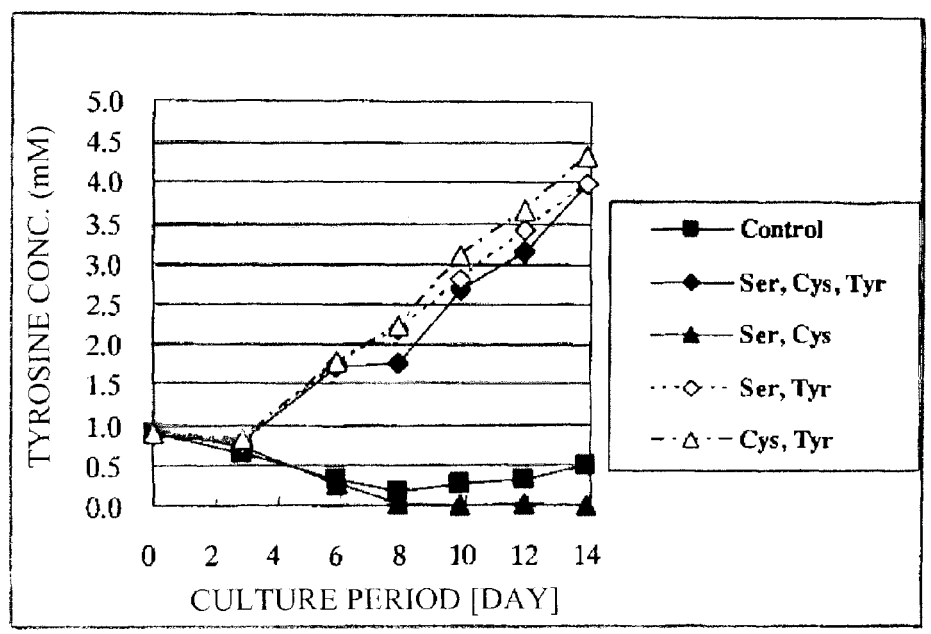
FIG. 15 shows transition of the tyrosine concentration during culture in a medium containing amino acids in high concentrations (Reference Example 3).

FIGS. 14 and 15 show transition in concentrations of serine and tyrosine, respectively, during the culture period for 14 days. In the control sample, the concentrations of serine and tyrosine were 0.63 mM and 0.34 mM, respectively, on the 5th day of the culture, and each concentration was 0.4 mM or less after the 7th day of the culture. However, in the culture using the fed-batch medium supplied with serine, the concentration of serine was maintained at 2 mM or more, and in the culture using the fed-batch medium supplied with tyrosine, the concentration of tyrosine was maintained at 1 mM or more.

The invention claimed is:

1. A method of culturing cells for producing a desired protein, comprising culturing cells capable of producing the protein using a culture solution containing an animal cell culture medium comprising a peptide consisting of 10 or fewer amino acids, or a salt thereof, wherein the amino acids are selected from serine, tyrosine, and cysteine.

2. A method of producing a desired protein, comprising producing the desired protein by culturing cells capable of producing the protein using an animal cell culture medium comprising a peptide consisting of 10 or fewer amino acids, or a salt thereof, wherein the amino acids are selected from serine, tyrosine, and cysteine.

3. The method according to claim 2, wherein the animal cell culture medium is added at the start of culture or is added in a fed-batch or continuous manner.

4. The method according to claim 2, wherein the cells are cultured by batch culture, repeated batch culture, fed-batch culture, repeated fed-batch culture, continuous culture, or perfusion culture.

5. The method according to claim 4, wherein the cells are cultured by fed-batch culture.

6. The method according to claim 5, wherein the animal cell culture medium is supplied to the culture solution by continual feeding repeated a plurality of times or continuous feeding.

7. The method according to claim 2, wherein the cells are transfected with a gene encoding a desired protein.

8. The method according to claim 7, wherein the desired protein is an antibody.

9. The method according to claim 2, wherein the cells are mammal cells.

10. The method according to claim 9, wherein the mammal cells are CHO cells.

11. A method for producing a drug, comprising producing a protein serving as an active ingredient by the method according to claim 2.

12. The method according to claim 2, comprising producing the desired protein by culturing cells capable of producing the protein using an animal cell culture medium comprising a tripeptide comprising serine, tyrosine, and cysteine, or a salt thereof.

13. The method according to claim 2, comprising producing the desired protein by culturing cells capable of producing the protein using an animal cell culture medium comprising a dipeptide comprising two kinds of amino acids selected from the group consisting of serine, tyrosine, and cysteine, or a salt thereof.

14. The method according to claim 12, wherein the cells are cultured by batch culture, repeated batch culture, fed-batch culture, repeated fed-batch culture, continuous culture, or perfusion culture.

15. The method according to claim 13, wherein the cells are cultured by batch culture, repeated batch culture, fed-batch culture, repeated fed-batch culture, continuous culture, or perfusion culture.

16. The method according to claim 12, wherein the cells are transfected with a gene encoding a desired protein.

17. The method according to claim 13, wherein the cells are transfected with a gene encoding a desired protein.

18. The method according to claim 12, wherein the cells are mammalian cells.

19. The method according to claim 13, wherein the cells are mammalian cells.

20. The method according to claim 2, further comprising isolating the desired protein from the culture medium.

* * * * *